United States Patent [19]

Collin

[11] 3,999,425
[45] Dec. 28, 1976

[54] METHOD AND APPARATUS FOR PREFORMING EXHAUST GAS EMISSION TESTS WITH VEHICLE ENGINES

[75] Inventor: Lars T. Collin, Molndal, Sweden

[73] Assignee: Lars Collin Consult AB, Molndal, Sweden

[22] Filed: Jan. 21, 1976

[21] Appl. No.: 650,883

Related U.S. Application Data

[63] Continuation of Ser. No. 439,941, Feb. 5, 1974, abandoned.

[30] Foreign Application Priority Data

Feb. 15, 1973  Sweden .......................... 73021123

[52] U.S. Cl. ............................. 73/116; 73/421.5 R
[51] Int. Cl.² ....................................... G01M 15/00
[58] Field of Search ........ 73/23, 116, 117, 421.5 R

[56] References Cited

UNITED STATES PATENTS

| 2,583,177 | 1/1952 | Hoekstra | 73/422 R |
| 3,406,562 | 10/1968 | Perna, Jr. et al. | 73/116 |
| 3,603,155 | 9/1971 | Morris et al. | 73/23 |
| 3,610,047 | 10/1971 | List et al. | 73/116 |
| 3,712,126 | 1/1973 | Campbell | 73/117 |
| 3,713,332 | 1/1973 | Herrbrich | 73/117 |
| 3,846,076 | 11/1974 | Henault | 73/116 |
| 3,864,964 | 2/1975 | Voelz | 73/116 |

*Primary Examiner*—Jerry W. Myracle
*Attorney, Agent, or Firm*—Holman & Stern

[57] ABSTRACT

For determining the emission contents of the exhaust gases of a vehicle internal combustion engine the idling engine is disengaged from the vehicle's driving transmission and is, during a fixed period of time, subjected to a series of load variations by momentarily increased charges of fuel to the engine. A certain fraction of the exhaust gas quantity generated during the mentioned period of time is drained or directed to a gas sampling unit, and this gas fraction is analyzed.

4 Claims, 5 Drawing Figures

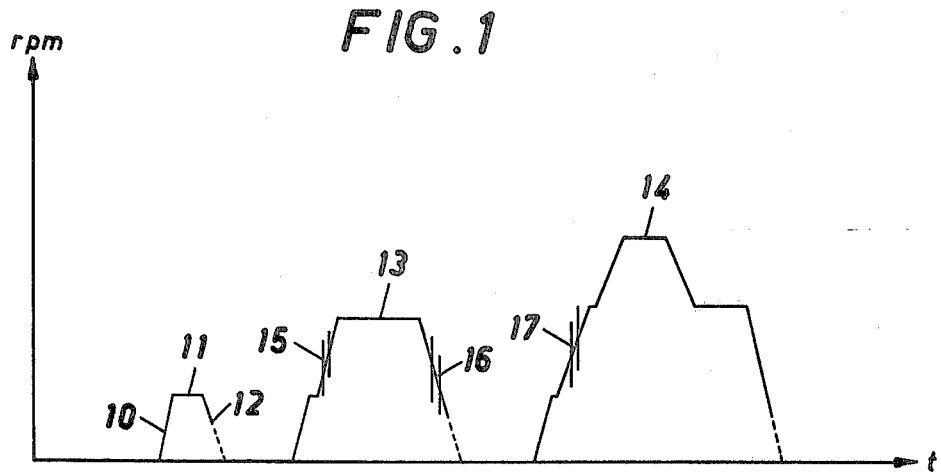
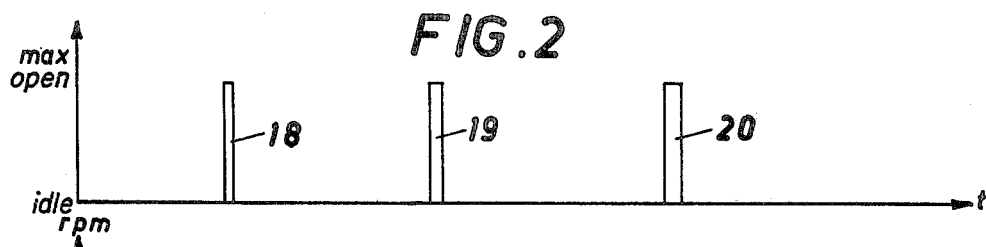
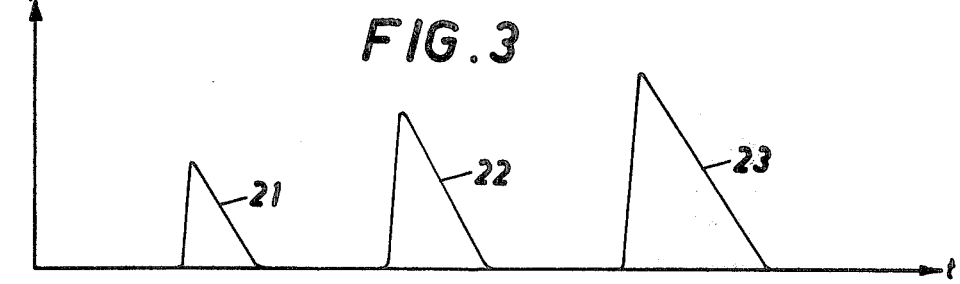
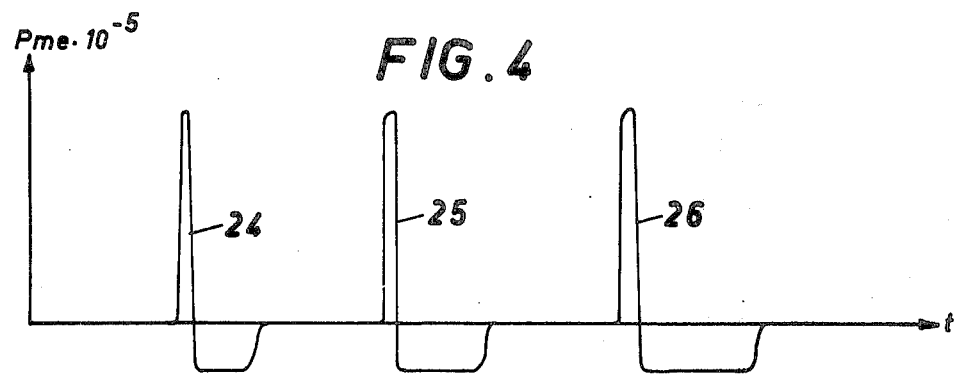

METHOD AND APPARATUS FOR PREFORMING EXHAUST GAS EMISSION TESTS WITH VEHICLE ENGINES

This is a continuation of application Ser. No. 439,941 filed Feb. 5, 1974 now abandoned.

BACKGROUND OF THE INVENTION

During the last decade, the internal combustion engine industry has more and more been forced to look into the problems related to the exhaust emission. The development is characterized by an increased, international legislative pressure on today's internal combustion engines for vehicles, in order to obtain lower and lower emission contents of CO, HC and $NO_x$, as well as of particles and noise.

National, comparatively uncomplicated testing cycles were first developed, simulating statistically established load sequences for engines in urban traffic. In connection with these test sequences, the contents of impurities in the exhaust gases were measured, and subsequently compiled in accordance with given rules or standards. These methods made possible an adjustment of the engine fuel supply system to low emissions within the tested, transient ranges and thus not giving a correct picture of the conditions during actual operation.

For that reason, it was, in some countries, decided to use a more complicated testing sequence, and simultaneously to take samples representing the accumulated emission in units of weight per distance for vehicles running in accordance with the new test cycle. One new testing sequence takes about 23 minutes to run, and requires a special gas sampling unit and a qualified gas analysis equipment, together with a chassi-dynamometer. The investment value of such an arrangement is, today, about $200,000 per unit, including erection and mechanical and analytical equipment.

This has created an instrument making it possible to check the cars produced and delivered, but is not convenient for practical supervision of the existing car park not, for example, it is evident that individual supervision of a large car park is impossible, if each test requires about half an hour for analysis, while at the same time qualified personnel and equipment is tied up for the same period. It are therefore important to find test procedures, which can make a rapid gas analysis possible. Carbon oxide tests have for some years been taken in connection with idling running during the annual checking of the Swedish car park. The idling sequence is, however, only part of the aforementioned cycles, and has the disadvantage that no content of nitrogen oxide can be traced, which can be correlated to the contents in the actual cycles. Neither are correlations between HC contents during idling, and HC contents during driving cycles satisfactory. In the international literature simplified driving cycles can be found directed toward making a simple supervision possible, but their common characteristics are that they require engine lead during controllable conditions on a chassi-dynamometer. The main part of the investment, discussed earlier, as well as the instrumentation requirements will remain, even if testing time might be reduced.

SUMMARY OF THE INVENTION

The present invention is directed toward an intermediate link between a detailed investigation with the chassi-dynamometer and a simple vehicle inspection.

It is based upon the fact that during actual driving cycles proposed, the heavy gas emissions depend upon transient procedures, accelerations and retardations, as well as idling periods. The actual, complicated driving cycles have the advantage, that stable conditions concerning temperatures of the exhaust gases and the engine will be obtained for different operational conditions, which also make possible a check of thermal or catalytic exhaust reactions. The method suggested contemplates considerations of the raw gas quality, i.e., the gas composition existing before subsequent thermal and catalytic reactors have started their action. An engine has an internal moment of inertia, meaning that an acceleration of the engine speed from idling requires a significant consumption of power within the engine itself during the acceleration sequence. By letting an engine accelerate by a defined fuel supply impulse to its maximum speed, normally defined as obtainable by constant acceleration (linear speed control), or some part thereof, a load sequence is obtained including acceleration under load as well as engine braking after the fuel supply period. This loading sequence can be repeated with different intensities according to a given pattern, and in that way both CO, HC and $NO_x$ emissions may be obtained with reasonable correlation to the more sophisticated tests including different coefficients for the different components.

The invention refers to a method for determining the emission contents of the exhaust gases of a vehicle engine which is characterized in that the idling engine, disengaged from the vehicle's driving transmission, during a fixed period of time is subjected to a series of load variations by momentarily increasing the fuel supply so the engine repeatedly will accelerate during some steps to about full maximum speed and during other steps to part thereof only, and immediately thereafter will be decelerated to idling speed, so that a certain fraction of the exhaust gas quantity generated during the mentioned period of time is collected at a gas sampling unit, and so that the total emission contents of the gas fractions gathered during the period of time are determined.

The invention also includes an apparatus for establishing the emission contents of the exhaust gases of a vehicle engine which is characterized in that it includes a device for operating the fuel supply system of the engine in accordance with a predetermined program to cause, during the fixed period of time, a number of fuel supply charges of different duration, none exceeding what is required to raise the speed of the engine to about maximum value, as well as a gas sampling unit for connection to the engine exhaust pipe, said unit having a sufficient volume to accumulate the portioned gas quantity without jeopardizing the test result by increased counter-pressure.

The sampling during the emission tests is assumed to be a draining of a given quantity fraction of the exhaust gases into a bag. This fraction can either be led through a gas analysing equipment or, in the most uncomplicated case, through an absorbing, indicating chemical mixture, where — by means of an already stipulated gradation or standard — it can be found if the vehicle is in satisfactory operating condition, or if a careful investigation according to earlier methods should be made. An application of these methods to find the cars violating existing rules (standards) could reduce the requirements of qualified sampling in an existing car parking lot by between one and two out of 10-potentials giving quite another aspect to economic requirements for supervising resources than was previously possible.

BRIEF DESCRIPTION OF THE DRAWINGS

FIG. 1 shows a part of an established test cycle,

FIGS. 2–4 show modifications in the throttle position, speed and mean engine pressure, respectively, during tests according to the invention.

DESCRIPTION OF A PREFERRED EMBODIMENT

Figure 5:
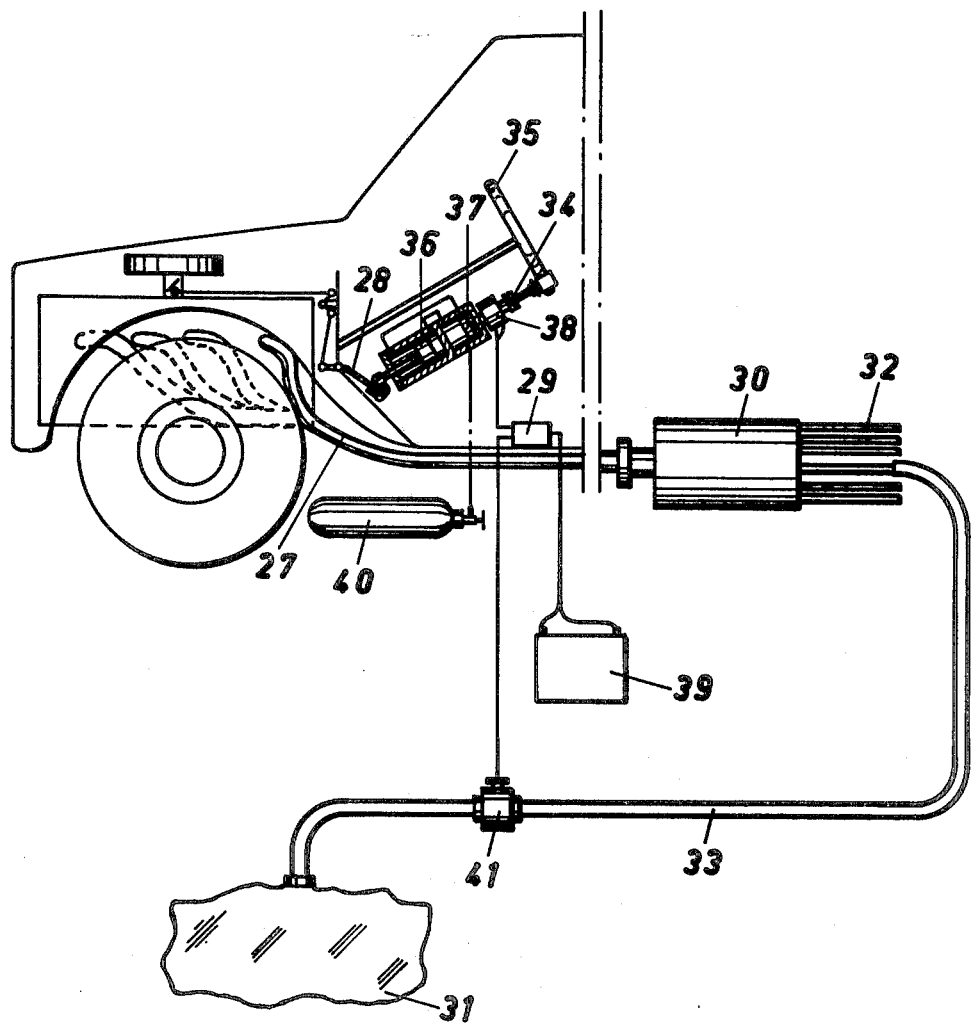
FIG. 5 shows a schematical view of the apparatus during use.

FIG. 1 illustrates speed modifications during a certain period of time in an established test cycle, aiming at simulating actual operational conditions, while the vehicle rests on a chassi-dynamometer.

The engine together with rotatable parts of the vehicle + the brake rollers of the chassi-dynamometer + the rotating counter weights, in total corresponding to the weight of the vehicle, is first accelerated during a certain time interval 10, subsequently operated at constant speed during a following interval 11, retarded during interval 12 to idling speed, and thereafter accelerated in a similar manner, but to various values as suggested at 13 and 14.

The testing cycle suggested here is based upon the idea that the inertia of the engine means a sufficiently large resistance for obtaining — with the engine disconnected from the driving transmission — representative test values, if the engine is rapidly accelerated to a certain speed range, and the fuel supply is then immediately reduced to what is required for idling.

In this way it is possible to obtain short test conditions, which momentarily are equivalent to sections 15, 16, 17 of the acceleration and deceleration curves in an established test cycle.

FIG. 2 shows modifications of the throttle position during a test in accordance with the invention. At predetermined intervals, which are sufficiently spaced to permit the engine, at each occasion, to return to its idling speed, a fuel supply impulse or change 18, 19 and 20, respectively of varying length (duration) is issued.

The impulses show stepwise increasing lengths, but this is purely illustrative. A real test includes several impulses, and their mutual sizes can be varied in different ways.

It is essential that none of the fuel impulses or charges has such a length that the engine will be operated at its maximum speed for any interval of time. It is merely the conditions prevailing during acceleration and deceleration that are interesting.

FIG. 3 shows modifications in motor speed as a consequence of the fuel impulses indicated in FIG. 2. It is obvious that both speed and operational time will increase from 21 to 23 as a consequence of the increased duration of the gas supply in this example.

Finally FIG. 4 shows basic changes 24, 25, 26 in the engine mean pressure during the occasions mentioned regard in FIG. 2.

FIG. 5 shows, very schematically, the apparatus used during the testing.

DESCRIPTION OF A PREFERRED EMBODIMENT

The exhaust pipe of a vehicle is denoted by 27, and the throttle operating pedal of the vehicle is denoted by 28.

For actuating the pedal a mechanical device 29 is provided, the details of which are not specified. This device will actuate the pedal in accordance with a predetermined program, so the engine — which is supposed to be idling — during a fixed period of time will obtain a certain number of fuel supply impulses or charges of varying lengths (duration). These impulses must — as outlined above — not have such a duration that the engine during any period of time will run at its maximum speed, or reach speeds which would damage its functions.

For operating the latter, an apparatus is used, which is capable of repeatedly issuing the predetermined fuel supply pulses or charges with a satisfactory consistent accuracy from one test sequence to another.

The apparatus may be designed in many ways and only the main components are shown, furthermore in a schematic manner. There is the master unit 29 preferably of electronic type, an exhaust volume portioning device 30, and a bladder-shaped receiver 31, preferably made of plastics. The latter is intended for connection to one of a number of outlet pipes 32 from the volume portioning device 30 by means of a hose 33.

A device for acting upon the gas pedal includes a rod 34, which is to be mounted between the steering wheel 35 and the floor therebelow. This rod carries a double acting, compressed air (pneumatic) motor 36, which is governed by a valve 37 operated by a solenoid 38 obtaining impulses from the master unit 29.

The latter is connected to a battery 39, and the compressed air motor is supplied with compressed air from a bottle 40, or from some other source. The hose 33 is provided with a solenoid valve 41, governed by signals from the electronic unit 29 to permit flow to the bag 31 during the test cycle only.

The means for supplying motive power to the unit 29 and to the servomotor 36 will depend upon local circumstances. The motor can be operated electrically, hydraulically or possibly mechanically, for instance by spring power. The motor furthermore may be located more closely to the motor so it acts directly upon a throttle lever.

The device 29 for issuing the basic signals may also be of arbitrary type. In order to be able to take care of cars of different sizes and types an electronic unit may be designed to be governed by punched cards or other information carriers, or possibly contain easily substituted printed circuit tablets.

The volume portioning device consists conveniently of a cylindrical receiver. To one of its ends a number of pipes 32 with carefully determined lengths and inner diameter are connected. A conduit 33 connected to bladder 31 is attached to the cylinder in equal pitch with above pipes 32. The diameter and the length of conduit 33 is so determined, that a practically constant volume fraction is transferred to the sampling bag within the actual flow range.

The counter-pressure is thus, within the measuring range, substantially like the one in the other pipes, the number and diameters of which will determine the size of the volume fraction. The bladder has such a volume, that it can accumulate the gas fraction divided off by the volume portioning device without causing a counter-pressure disturbing the sampling.

It is important that the gas sampling unit during the strongly varying flow intensities of the test divides the quantities in constant proportions between total exhaust gas quantity and sample quantity, respectively. Instead of filling a bladder the separated fraction can be led directly to a measuring device.

I claim:

1. A method of testing for determining the emission contents of the exhaust products of internal combustion engines, the improvement comprising the steps of: (a) running an internal combustion engine of a vehicle at an idling speed with the driving transmission disengaged during the test; (b) during a fixed period of time, utilizing the inertia of the internal combustion engine as a braking factor, repeatedly subjecting the engine to a series of load variations by momentarily varying the fuel supply to the idling engine and repeatedly accelerating the engine against its own inertia to speeds within the range below maximum speed and after an acceleration permitting the engine to decelerate towards the initial idling speed; and (c) controlling the collection of a proportionate fraction of the exhaust products in a sample receiver unit in response to variations of the fuel supply.

2. An apparatus for determining the emission contents of the exhaust of a disengaged internal combustion engine of a vehicle including, in combination, a master control unit for automatically operating the fuel supply system of the disengaged engine according to a predetermined program; means for connection to the engine exhaust system including means for dividing the exhaust into proportionate parts; and a receiver operatively connected to said means for dividing the exhaust for capturing a proportionate part of the entire exhaust during a test cycle, the improvement comprising: valve means operatively connected between said receiver and means for dividing said exhaust for controlling exhaust product flow into said receiver; the master control unit including a program selected so as to hold the engine, when out of driving relationship, at idling speed and to cause, during a fixed period of time, a number of fuel supply sequences, below maximum speed, consisting of a few accelerations-retardations, so that there is a somewhat extended operation period before dropping down to idling, during which the fuel supplied does not exceed that amount which is required to raise the speed of the engine against its own inertia to its full speed, said program spacing the fuel supply sequences sufficiently to permit the engine to return to the idling speed due to internal engine power losses; means to issue a first signal at the beginning of the fixed period of time to open said valve means; and means to issue a second signal at the termination of the fixed period of time to close said valve means.

3. The apparatus according to claim 2 including a double-acting, pneumatic motor operatively connected to a fuel control pedal of the vehicle for operating the fuel supply to the internal combustion engine, a solenoid control operatively connected to the pneumatic motor for operating the same, the master control unit including electronic means for issuing signals for activating the solenoid control according to the program of the master control unit.

4. An apparatus for determining the emission contents of the exhaust of an internal combustion of a vehicle including, in combination, a master control unit for automatically operating the fuel supply system of the engine according to a predetermined program; means for connection to the engine exhaust system including means for dividing the exhaust into proportionate parts and a receiver operatively connected to said means for dividing the exhaust for capturing a proportionate part of the entire exhaust during a test cycle, the improvement comprising: valve means operatively connected between the receiver and means for dividing said exhaust for controlling exhaust product flow into said receiver; the master control unit including a program selected so as to hold the engine, when out of driving relationship, at idling speed and to cause, during a fixed period of time, a number of fuel supply variations during which the fuel supplied does not exceed that amount which is required to raise the speed of the engine against its own inertia to its full speed, said program spacing fuel supply sequences, below maximum speed, consisting of a few accelerations-retardations, so that there is a somewhat extended operation period before dropping down to idling, sufficient to permit the engine to return to the idling speed due to internal engine power losses; and means to issue a first signal at the beginning of a fixed period of time to open said valve means and means to issue a second signal at the termination of the fixed period of time to close said valve means; the gas proportioning means including a chamber connectable to the engine exhaust system and comprising a plurality of equal-resistance outlets open to ambient air, and conduit means for connecting the receiver to said chamber, the receiver being so arranged that it, together with the conduit means, within the actual flow gas range, have substantially the same resistance, as any one of the open outlets of the chamber.

* * * * *